US011131665B1

(12) United States Patent
Beckley

(10) Patent No.: US 11,131,665 B1
(45) Date of Patent: *Sep. 28, 2021

(54) METHOD FOR EVALUATING URINE OF A SUBJECT TO ESTIMATE THE FERTILE WINDOW

(71) Applicant: MFB Fertility, Inc., Erie, CO (US)

(72) Inventor: Amy Beckley, Erie, CO (US)

(73) Assignee: MFB Fertility, Inc., Erie, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/308,149

(22) Filed: May 5, 2021

Related U.S. Application Data

(63) Continuation of application No. PCT/US2020/040600, filed on Jul. 2, 2020, which is a continuation-in-part of application No. 16/732,766, filed on Jan. 2, 2020, now Pat. No. 11,029,321, which is a continuation-in-part of application No. 16/544,554, filed on Aug. 19, 2019, which is a continuation-in-part of application No. 16/381,229, filed as application No. PCT/US2018/068027 on Dec. 28, 2018.

(60) Provisional application No. 63/023,116, filed on May 11, 2020, provisional application No. 62/720,953, filed on Aug. 22, 2018.

(51) Int. Cl.
*G01N 33/543* (2006.01)
*A61B 10/00* (2006.01)
*G01N 33/74* (2006.01)
*G01N 33/76* (2006.01)

(52) U.S. Cl.
CPC ..... *G01N 33/54306* (2013.01); *A61B 10/007* (2013.01); *A61B 10/0012* (2013.01); *G01N 33/743* (2013.01); *G01N 33/76* (2013.01); *G01N 2333/575* (2013.01); *G01N 2333/59* (2013.01); *G01N 2800/36* (2013.01); *G01N 2800/362* (2013.01)

(58) Field of Classification Search
None
See application file for complete search history.

(56) References Cited

U.S. PATENT DOCUMENTS

| | | | |
|---|---|---|---|
| 4,450,239 A | 5/1984 | Chatterton |
| 9,386,221 B2 | 7/2016 | Kauniskangas et al. |
| 9,787,815 B2 | 10/2017 | Erickson et al. |
| 2006/0121626 A1 | 6/2006 | Imrich |
| 2010/0312137 A1 | 12/2010 | Gilmour et al. |
| 2013/0273563 A1 | 10/2013 | Ehrenkranz |
| 2015/0094227 A1 | 4/2015 | McCarthy et al. |
| 2015/0304555 A1 | 10/2015 | Ehrenkranz |
| 2015/0338387 A1 | 11/2015 | Ehrenkranz |
| 2016/0139156 A1 | 5/2016 | Lakdawala |
| 2016/0167042 A1 | 6/2016 | Tyrrell et al. |
| 2016/0178607 A1 | 6/2016 | Husheer et al. |
| 2017/0007215 A1 | 1/2017 | Podoly |
| 2017/0011194 A1 | 1/2017 | Arshad et al. |
| 2018/0321251 A1 | 11/2018 | Beckley |
| 2020/0141954 A1 | 5/2020 | Beckley |

FOREIGN PATENT DOCUMENTS

| | | |
|---|---|---|
| CN | 104697938 B | 4/2018 |
| EP | 0656118 B1 | 6/1995 |
| EP | 2788764 A1 | 10/2014 |
| EP | 2839264 A1 | 2/2015 |
| EP | 2861991 A1 | 4/2015 |
| EP | 3052944 A1 | 8/2016 |
| WO | 1995016920 A1 | 6/1995 |
| WO | 9839657 A1 | 9/1998 |
| WO | 2007/049157 A2 | 5/2007 |
| WO | 2016/115608 A1 | 7/2016 |
| WO | 2016/166415 A1 | 10/2016 |
| WO | 2017/058827 A1 | 4/2017 |
| WO | 2017/180909 A1 | 10/2017 |

OTHER PUBLICATIONS

Santoro et al., Obstet Gynecol Clin North Am. Author manuscript; available in PMC Sep. 1, 2012—15 pages total (Year: 2012).*
Su et al., Minerva Ginecol. Author manuscript; available in PMC Nov. 12, 2013—9 pages total (Year: 2013).*
Mesen, T.B., et al., "Progesterone and the Luteal Phase: A Requisite to Reproduction," Obstetrics and Gynecology Clinics of North America, Mar. 2015, vol. 42, No. 1, pp. 135-151; p. 3, 4th paragraph; p. 4, 3rd paragraph; p. 6, 5th paragraph; p. 7, 2nd paragraph; p. 9, 2nd paragraph; DOI: 10.1016/j.ogc.2014.10.003.
MFB Fertility Inc., "How do Ovulation Double Check Tests Work," Oct. 2, 2017 [retrieved on Feb. 25, 2019]. Retrieved from the internet; timestamps 0:07-0:45, 1:00-2:30.
Munro, C.J., et al., "Relationship of Serum Estradiol and Progesterone Concentrations to the Excretion Profiles of Their Major Urinary Metabolites as Measured by Enzyme Immunoassay and Radioimmunoassay," Clinical Chemistry, Jun. 1991, vol. 37, No. 6, pp. 838-844; p. 840, 2nd column, 3rd paragraph; Table 2.
PCT International Search Report with attached Written Opinion of the International Searching Authority for International Application No. PCT/US18/68027, dated Mar. 26, 2019, 16 pages.
R. Leiva, M. McNamara-Kilian, H. Niezgoda, et al., Pilot observational prospective cohort study on the use of a novel home-based urinary pregnanediol 3-glucuronide (PDG) test to confirm ovulation when used as adjunct to fertility awareness methods (FAMs) stage 1. BMJ Open 2019.

(Continued)

*Primary Examiner* — Christina M Borgeest
(74) *Attorney, Agent, or Firm* — Hall Estill Attorneys at Law; Jeffrey R. Schell

(57) ABSTRACT

Disclosed herein are devices, systems, methods and kits for performing immunoassay tests to detect for at least progesterone or analytes of progesterone on a sample in association with diagnosing problems and issues associated with corpus luteum functionality. The immunoassay devices and methods may be used in conjunction with diagnostic reader systems and/or a base unit for obtaining a sensitive read-out of the immunoassay results. The immunoassay devices and methods may utilize a competitive binding-like assay and a sandwich binding assay to detect at least progesterone or analytes of progesterone in a sample.

8 Claims, 6 Drawing Sheets

(56) References Cited

OTHER PUBLICATIONS

S. Kerrigan and W. Phillips, Comparison of ELISAs for Opiates, Methamphetamine, Cocaine Metabolite, Benzodiazepines, Phencyclidine, and Cannabinoids in Whole Blood and Urine. Clinical Chemistry 47:3 540-547 (2001).
GooglePlay, "DaysyView" Valley Electronics, Aug. 20, 2015, p. 1, Paragraphs 1 and 3 (5 pages).
PCT International Search Report with attached Written Opinion of the International Searching Authority for International Application No. PCT/US20/40600, dated Nov. 20, 2020, 13 pages.

* cited by examiner

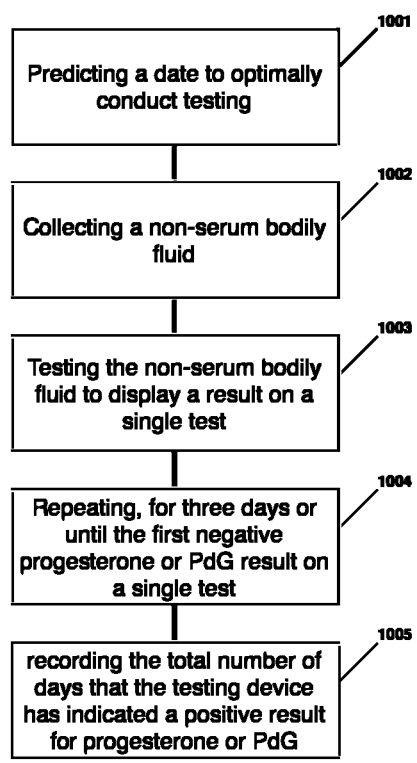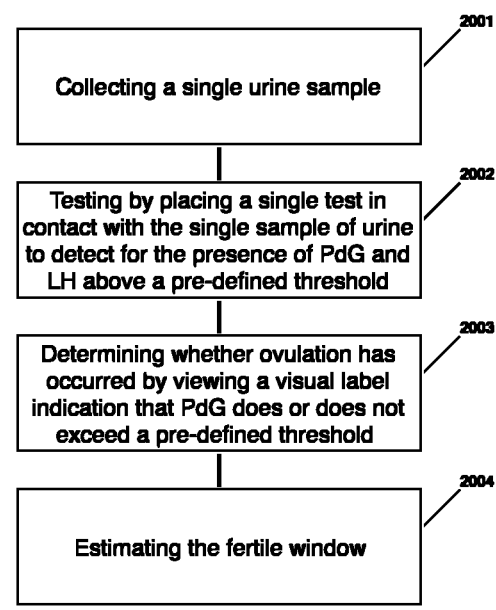
Fig. 1
Fig. 2

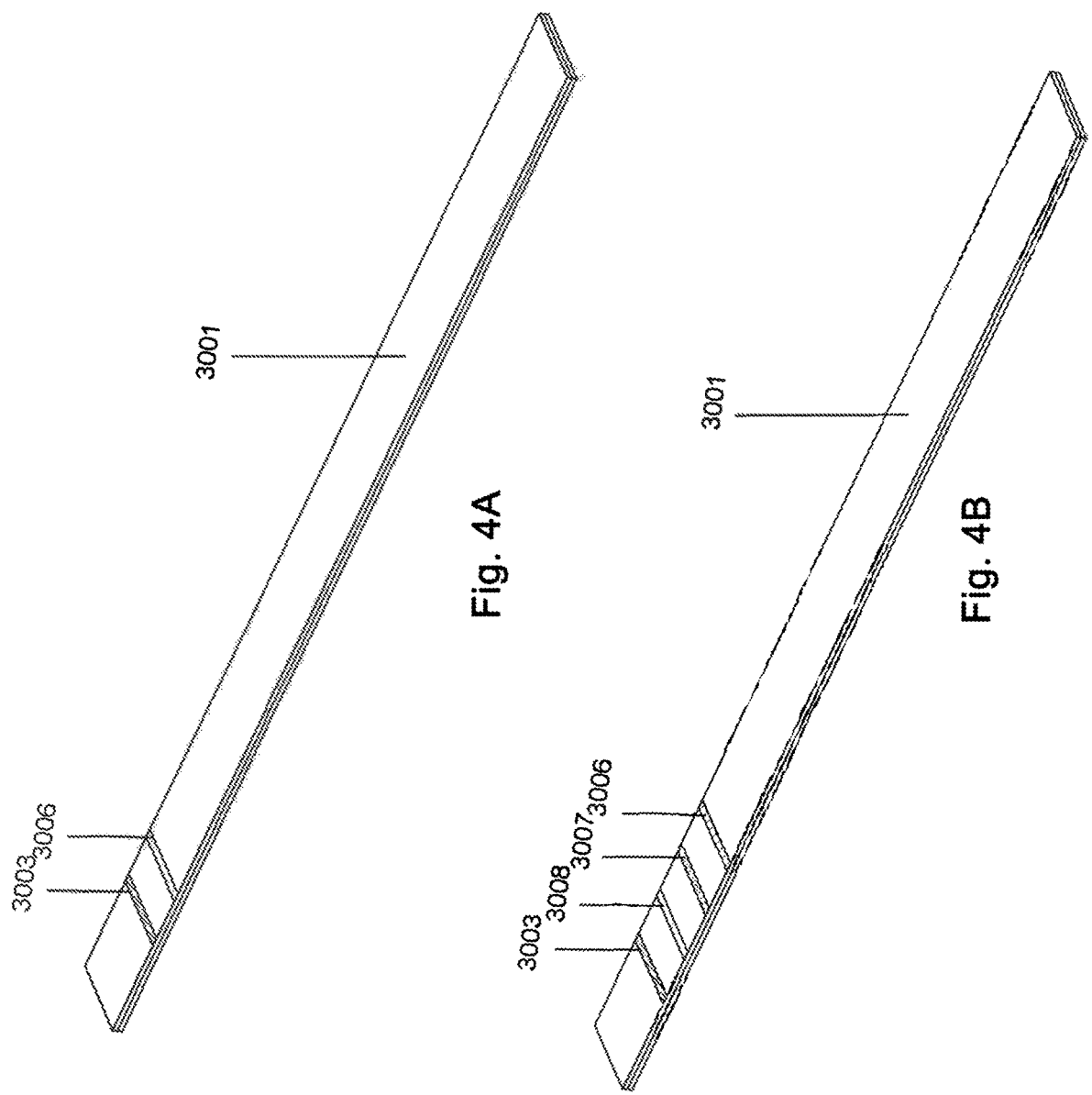

METHOD FOR EVALUATING URINE OF A SUBJECT TO ESTIMATE THE FERTILE WINDOW

CROSS-REFERENCE TO RELATED APPLICATIONS

This application is a continuation-in-part of U.S. Non-provisional patent application Ser. No. 16/732,766, filed on Jan. 2, 2020, with priority claimed thereto and hereby incorporated by reference in its entirety. This application claims the benefit of U.S. Provisional Patent Application 63/023,116 filed on May 11, 2020, with priority claimed thereto and hereby incorporated by reference in its entirety.

FIELD OF THE INVENTION

The present invention relates to the field of hormone diagnostics. More specifically, the present invention relates to urine based lateral flow assays for the detection of hormones relevant to the corpus luteum and methods of interpretation and digital quantification thereof.

BACKGROUND OF THE INVENTION

The Corpus Luteum is a mass of cells that forms in an ovary. During ovulation, an egg is released from a dominant follicle. Following the release of the egg and subsequent fertilization, the follicle seals itself off and forms the Corpus Luteum. The Corpus Luteum produces the hormone progesterone during the luteal phase and during early pregnancy. The luteal phase is the part of the menstrual cycle that occurs after ovulation. It typically lasts 12-16 days, during time which the Corpus Luteum functions. Following conception, the Corpus Luteum functions to produce progesterone until the placenta can produce adequate levels to sustain the pregnancy, which usually occurs between 7 and 9 weeks of pregnancy. Progesterone is essential during early pregnancy because it allows the uterus to grow without having contractions, stabilizes the lining of the uterus, and improves blood flow and oxygen supply.

The Corpus Luteum a key anatomical structure associated with menstrual cycle timing. Women often attempt to chart their menstrual cycles with the aid of home use urine or saliva tests configured to detect Luteinizing Hormone (LH). However, the presence of LH only predicts the onset of ovulation and only indicates one portion of the menstrual cycle. The presence of LH does not confirm that the Corpus Luteum is functioning properly to actually release an egg. Only the corresponding release of progesterone beyond a threshold level indicates that an egg has been released. It would therefore be desirable to have an efficient and accurate method to track progesterone non-invasively and without delays associated with third party review of testing results to better understand menstrual cycle timing and Corpus Luteum functionality.

To accurately chart an entire menstrual cycle, a woman must understand the ovulation date as indicated by strips that detect for the presence of lutenizing hormone, counting days from the date of beginning menstruation, or measuring basal body temperature, for instance. Therefore, a progesterone test that does not deliver results on the same day of the test (i.e. a test that requires delivery of a sample to a lab) is not practical to allow a woman to utilize a method to measure and track her progesterone on a daily basis. The excessive waiting for the results of such lab-based progesterone tests, in addition to multiplying anxiety, prevent accurate tracking because the time that it takes to deliver results presents a picture of what occurred in a past part of the menstrual cycle, not a current part of the menstrual cycle. Thus, the use of progesterone testing that requires multiple days for results does not allow for accurate mapping of the cycle until such time that the information loses its value. It would therefore be desirable to have a method that incorporates immediate progesterone testing and tracking to effectively chart a menstrual cycle and immediately utilize the results.

The Corpus Luteum is supported and maintained by lutenizing hormone (LH) initially, and then the pregnancy hormone human chorionic gonadotrophin (HCG). The corpus luteum begins to decrease in size at around 7-9 weeks of pregnancy. When fertilization or implantation do not occur, the Corpus Luteum will begin to break down 10-14 days following ovulation. This causes a decline in estrogen and progesterone levels, leading to the start of another menstrual period.

Corpus Luteum problems often result from the insufficient production of progesterone or if progesterone production ends too soon. If progesterone is absent or levels are too low, irregular and heavy menstrual bleeding can occur. Lack of progesterone in the bloodstream can mean the ovary has failed to release an egg at ovulation, as can occur in women with polycystic ovary syndrome.

The evaluation of Corpus Luteum functionality is important in association with diagnosing and preventing fertility-related problems. A drop-in progesterone during pregnancy can result in a miscarriage and early labor. However, there are available treatments to address related conditions. For instance, those at risk of giving birth too soon can be given a synthetic form of progesterone to delay the onset of labor. Therefore, it would be desirable to have a method that allows for the instantaneous review of results showing progesterone above or below a threshold level over a period of days incorporating a specifically configured device that allows for the delivery of immediate or near-immediate results on each day to alert a pregnant woman immediately that a miscarriage may be imminent without progesterone supplementation.

Corpus Luteum function can also be evaluated by an accurate measurement of progesterone. As a temporary endocrine gland that the female body produces after ovulation during the second half of the menstrual cycle, the Corpus Luteum secretes progesterone, impacting the blood progesterone level. For a woman who menstruates, her blood progesterone level should be low at the beginning of each menstrual cycle. It should peak several days after she has ovulated properly. Then it should fall back to low levels, unless the woman has become pregnant in which case progesterone will continue to be secreted to prevent uterine contractions that may disturb the growing embryo. Ranges of these levels remain generally consistent among properly ovulating females of a particular population, therefore evaluation of these levels to determine whether the test results correlate with the expected progesterone range of a particular population can be used to either confirm proper Corpus Luteum functioning, among other valuable information. However, such results have been only generally available via a blood test or mail-in kit, which limits the availability of repetitive testing over a period of several subsequent days.

The main mechanism for evaluating the production of progesterone is via a serum progesterone test, or blood test. During such procedure, a medical professional collects a sample of the patient's blood in their office or sends the patient to another site to have blood drawn. Typically the test is then sent to an external lab for testing, a process that typically requires several days to complete. Serum progesterone levels are typically measured in nanograms per milliliter (ng/mL) in the United States of America. Once results are generated from the laboratory, the laboratory will send them to the patient's medical professional, who will generally relay them back to the patient. Many inconveniences to the patient arise from prior art methods of evaluating progesterone via serum draws on a recurrent basis. For many patients, particularly patients living in rural areas, access to blood labs requires a significant expenditure in time and travel costs. Also, for many patients, a visit to a blood testing facility requires missed work. For all patients, the pain and invasive nature of blood testing represents an opportunity for inventive improvement. However, for serum progesterone testing and any other progesterone test that generally requires more than one day for sample collection and evaluation, collection of results on subsequent days without near-instantaneous results for each sample evaluation is impractical for the purposes of accurate corpus luteum evaluation. The slow nature of receiving such test results makes it impractical for evaluation of corpus luteum function that can usefully be applied by the subject for diagnosis and corrective efforts on a continuous basis. Therefore, it would be desirable to have a method for testing for corpus luteum functionality where results may efficiently be collected on subsequent days to correct the drawbacks of previously utilized technologies by utilizing a technology that allows for aggregation and evaluation of progesterone testing results on a near-instantaneous basis in subsequent days.

What is required for the process to function is a test that evaluates urine for the presence of progesterone or progesterone analytes beyond a threshold of 5 micrograms per milliliter (ug/mL) during the timeframe of 7-10 days past ovulation that allows a user to gain near-instantaneous results by evaluation of urine or saliva on a daily basis without visitation to a clinic. Such specifically configured test has not been available until the recent development of the Proov rapid response urine progesterone test by MFB Fertility, Inc., elements of which are further described in PCT Patent Application PCT/US18/68027 and U.S. patent application Ser. No. 16/381,229, each of which are hereby incorporated by reference in their entirety. What also would be desirable is a saliva test configured to sample saliva and provide near-instantaneous results for the presence of progesterone at or above a level corresponding to proper Corpus Luteum functioning to a user as a non-urinary alternative, without requiring the user to deliver the results to a lab for interpretation.

Moreover, existing methods often require direction by a physician for evaluation. Typically, a woman suffering from infertility would seek guidance from a physician. In many cases, physicians either choose or are prohibited by insurance companies from providing treatment until the patient can document that she has tried for more than twelve months to conceive. When the physician provides treatment, often the first evaluation involves determining whether there is a blocked tube, sperm deficiency, anatomical structural abnormality, or genetic factors prior to evaluating hormonal problems more generally associated with Corpus Luteum functionality. Each of these issues requires time to evaluate. Due to the biological clock, women often at best suffer anxiety as the diagnostic process progresses, and at worst move from a phase in their lives where they can conceive and maintain pregnancy to a phase where they cannot. Thus, it remains desirable for an alternative method to empower women to more rapidly and independently understand and diagnose potential Corpus Luteum functionality problems.

A variety of other problems result from improper Corpus Luteum functioning. For instance, improper luteal function is linked to mood changes and depression. Improper luteal function has also been linked to weight gain, brittle bones, memory loss, PMS, anxiety, perimenopause, and increased risk of ovarian and breast cancer. It would therefore be desirable to have an efficient method to detect improper Corpus Luteum functioning following or preceding the onset of such maladies to allocate appropriate treatment resources.

BRIEF SUMMARY OF THE INVENTION

The present inventor has developed a method for evaluating a non-serum bodily fluid daily over a period of multiple days for the presence of progesterone or an analyte of progesterone beyond a threshold to detect for suboptimal corpus luteum functioning. The present inventor has relatedly developed a test device useful in association with evaluating corpus luteum functioning.

BRIEF DESCRIPTION OF THE SEVERAL VIEWS OF THE FIGURES

FIG. 1 shows method steps associated with a method to evaluate corpus luteum functionality.

FIG. 2 shows method steps associated with a method to estimate the fertile window in association with corpus luteum functionality.

FIG. 4A depicts an embodiment of the test strip comprising a single capture region. FIG. 4B depicts an embodiment of the test strip comprising a plurality of capture regions.

DETAILED DESCRIPTION OF THE INVENTION

The present inventor has developed a method for evaluating a non-serum bodily fluid daily over a period of multiple days for the presence of at least progesterone or an analyte of progesterone beyond a threshold to detect for suboptimal corpus luteum functioning.

The method addresses the drawbacks of previous methods of corpus luteum evaluation. The present inventor has discovered a method addressing at least one specific drawback associated with blood serum testing for progesterone, useful in association with evaluating corpus luteum functionality, specifically that progesterone in the bloodstream is cyclical by nature. The cycle of serum progesterone happens as result the corpus luteum forming a part of the endocrine system. More specifically, the corpus luteum secretes progesterone in waves responding to changes in serum progesterone levels. Therefore, as the present inventor has recognized, a single point serum progesterone test may not accurately present an accurate representation of corpus luteum functionality, as it presents the progesterone level at only a single point of time, rather than reporting a trend of serum progesterone levels.

To address this shortcoming, the present inventor devised a method utilizing newly available single tests configured to evaluate urine for the presence of at least progesterone or an analyte of progesterone (such as PdG), which may comprise one or more test strips 3001 configured to evaluate non-serum bodily fluids, such as those further described in U.S. patent application Ser. No. 16/544,554 filed on Aug. 19, 2019, which is incorporated by reference herein in its entirety. The present inventor has also recognized that the novel configuration of such single tests are well suited for utilization with additionally configured base units and processing devices to create additional functionality as described elsewhere herein.

Figure 7:
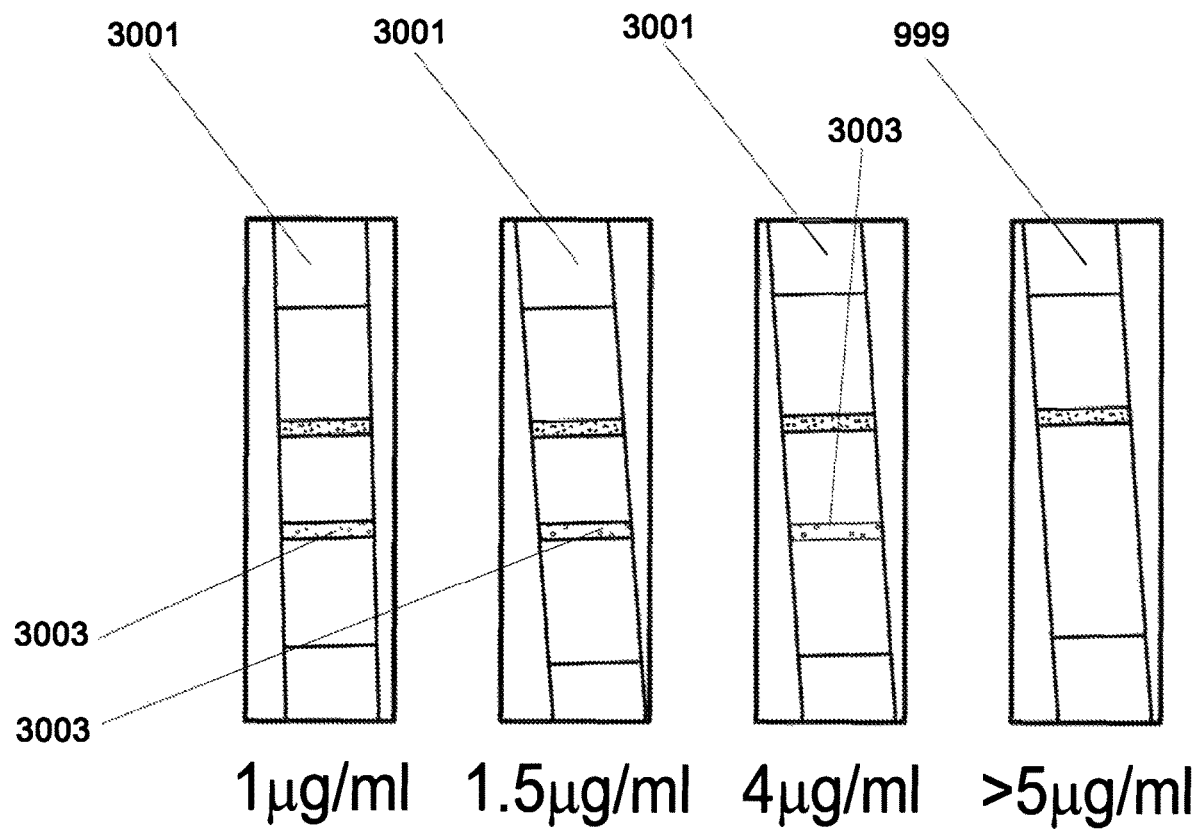
FIG. 7 depicts exemplary values for PdG concentration associated with a fluid applied to a lateral flow assay configured to detect for the presence of PdG in the fluid in an embodiment of the invention.

FIG. 7 depicts exemplary visual indications displayed on a lateral flow assay configured to detect PdG in an applied fluid at a threshold of 5 µg/ml, following the application of a fluid containing varying concentrations of PdG. As can be seen from the drawing, a positive result above 5 µg/ml is determinable when only one line is visible on the lateral flow assay.

The present inventor devised a method utilizing newly available single tests configured to evaluate urine for the presence of at least progesterone or an analyte of progesterone (such as PdG), which may comprise one or more test strips 3001 configured to evaluate non-serum bodily fluids, such as those further described in U.S. patent application Ser. No. 16/544,554 filed on Aug. 19, 2019, which is incorporated by reference herein in its entirety. The present inventor recognizes that due to variations in the ability of different populations to metabolize progesterone in urine, the 5 µg/ml threshold is not always the appropriate threshold. Therefore, various embodiments of the test strip 3001 are configured to display a positive or negative result based on pre-defined thresholds of a PdG level of a value selected from values within the range of 3 µg/ml-20 µg/ml. Results, in association with embodiments of the invention, demonstrate high concentrations of PdG by depiction in the testing zone of the test strip 3001 of no visually detectible line; and medium concentrations of PdG by depiction in the testing zone of the test strip 3001 of a faint line; and low or zero concentrations of PdG by depiction in the testing zone of the test strip 3001 of a dark line. In the preferred embodiment, a positive result is indicated by the visual display of one colored line on the test strip 3001, indicating the presence of PdG above the pre-defined threshold within the urine test sample applied to the test strip 3001. In an example depicted in FIG. 7., a positive result of >5 µg/mL is indicated on the positive test strip 999 where the control line is visually perceptible to the naked eye and there is no line visually perceptible in the testing zone of the positive test strip 999. In the preferred embodiment, a negative result is indicated by the visual display of two colored lines on the test strip 3001, indicating the absence of PdG above the pre-defined threshold within the urine test sample applied to the test strip 3001. In an example depicted in FIG. 7., a negative result of <5 µg/mL is indicated where the control line is visually perceptible to the naked eye and there is another visually perceptible line in the testing zone of the test strip 3001. Therefore, in one example of the invention, urine samples with a concentration of <5 µg/ml PdG applied to the test strip 3001 will show two lines, indicating a negative result, and urine samples with a concentration of >5 µg/ml PdG applied to the test strip 3001 will only show one line, indicating a positive result. Therefore, in various embodiments of the invention, the present inventor has recognized that the test strip 3001 in a configuration reproducibly produces a negative test result if the PdG level in tested urine is below approximately 5 µg/ml; and the test strip 3001 in a configuration reproducibly produces a positive test result if the PdG level in tested urine is above approximately 5 µg/ml. The present inventor recognizes that due to variations in the ability of different populations to metabolize progesterone in urine, the 5 µg/ml threshold is not always the appropriate threshold. Therefore, various embodiments of the test strip 3001 are configured to display a positive or negative result based on pre-defined thresholds of a PdG level of a value selected from values within the range of 3 µg/ml-20 µg/ml. The present inventor has also recognized that the novel configuration of such single tests are well suited for utilization with additionally configured base units and processing devices to create additional functionality as described elsewhere herein. In association with the invention, a properly functioning corpus luteum is evidenced by a trend indicating the presence of a progesterone analyte at a threshold selected from a range inclusive of 3-20 µg/ml for at least two days during the period of 7-10 days past ovulation.

Figure 5A:
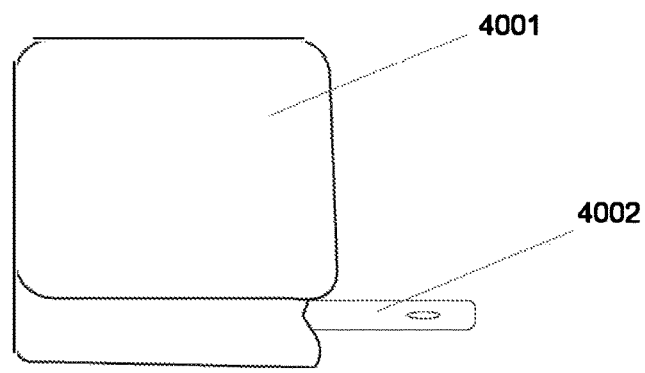
FIGS. 5A and 5B depict embodiments of a base unit.
Figure 5B:
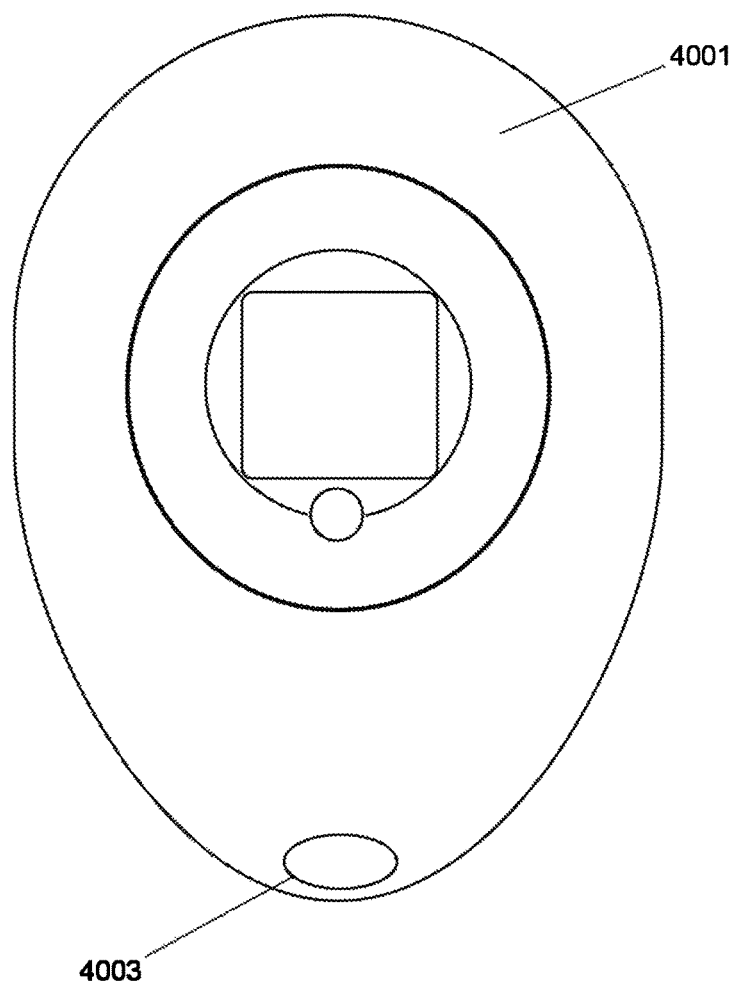

In association with the various systems and methods described herein, the test strip 3001 configured to evaluate urine for the presence of at least progesterone or an analyte of progesterone (e.g., PdG) optionally is configured such that the first capture region is configured such that, when used with a base unit, a first optical signal (e.g., a fluorescent signal) is capable of being detected at the first capture region. It is a teaching of an embodiment of the present invention for the test strip 3001 to optionally incorporate one or more additional testing zones beyond the testing zone configured to analyze urine for the presence of PdG, each additional testing zone specifically configured to evaluate urine for the presence of an item selected from the group consisting of LH, HCG, FSH, Testosterone and/or Estrogen or analytes thereof, such as E3G. The first optical signal may be a readout for the amount of progesterone analyte (e.g., PdG) in the sample, for example, by detecting the amount of first detection reagent bound to the first capture reagent. In such cases, the first optical signal increases when the amount of first analyte present in the sample is low, and the first optical signal decreases when the amount of first analyte present in the sample is high. In an embodiment of the invention, the test strip 3001 is further configured to additionally evaluate urine for the presence of estrone-3-glucuronide (E1G or E3G). In an embodiment, hormones and/or analytes such as LH and E3G may be measured simultaneously with PdG via a system comprising a specially configured single test strip 3001 capable of evaluating urine for the presence of PdG and other hormones and analytes, especially LH and E3G. Likewise, it is a teaching of an embodiment of the invention to provide at least one test strip 3001 capable of evaluating urine for at least the presence of LH and at least one second test strip capable of evaluating urine for at least the presence of PdG in association with the methods and other teachings herein. Estrone-3-glucuronide (also referred to as estrone glucuronide, E1G or E3G) is a principal metabolite of E2. The urinary levels of E3G correspond to the serum levels of E2. In an embodiment, a second (or subsequent) optical signal may indicate the presence or absence of estrone-3-glucuronide in the applied sample of urine from a subject. As the detection of estrone-3-glucuronide (or estrogen) is indicative of the opening of the fertile window, whereas in contrast no detection of estrone-3-glucuronide is indicative that the fertile window has not occurred. For example, in embodiments of the invention it is advantageous to interpret the rise (or initial detection of) estrone-3-glucuronide in a subject as confirmatory or predictive of the opening of the fertile window of the subject. As such, the second (or subsequent) optical signal may be a readout for the amount of estrone-3-glucuronide in the sample of urine, for example, by detecting the amount of second detection reagent bound to the second capture reagent. In such embodiment, the second (or subsequent) optical signal may take place in the second capture region, for example the second optical signal 3007 as indicated by FIG. 4B. The optical signal at the first capture region may be proportional to the amount of first analyte present in the sample. In various aspects, the capture zone further comprises a second capture region configured to produce an optical signal likewise corresponding to the presence or absence of a second analyte. In various aspects of the systems and methods herein, the test strip 3001 is configured for utilization in conjunction with a base unit 4001, for example a base unit depicted by FIG. 5A or FIG. 5B, together comprising a diagnostic test system. In such configuration, the observable positive result provided on the membrane of a lateral flow assay is obtained in association with the optical reader of such diagnostic test system. In various embodiments, the optical reader may comprise the camera of a smart phone. In various embodiments of the invention, a base unit 4001 associated with a diagnostic test system as described herein comprises the optical reader.

In one aspect, a diagnostic test system is provided comprising: a housing, comprising: a) a port for receiving an assay device, said assay device comprising two or more capture regions; b) a reader comprising: i) one or more light sources for illuminating said two or more capture regions; ii) one or more light detectors for detecting optical signals from said two or more capture regions; and c) a data analyzer having one or more processors configured to: A) receive said optical signals; and determine an amount of at least a first analyte and a second analyte present in a biological sample based on said optical signals, wherein an optical signal of a first of said two or more capture regions increases with decreasing amounts of said first analyte present in said biological sample, and an optical signal of a second of said two or more capture regions increases with increasing amounts of said second analyte present in said biological sample.

The diagnostic test system may include a housing for containing the components of the system. The housing can be constructed of any suitable material. The housing may be configured to receive an immunoassay device configured to detect for at least the presence or absence of progesterone or a progesterone analyte of the disclosure. For example, the housing may include a port or opening for receiving the immunoassay device configured to detect for at least the presence or absence of progesterone or a progesterone analyte. The system may further include, contained within the housing, a reader device. The reader device may include one or more light sources for illuminating the immunoassay device or a region of the immunoassay device configured to detect for at least the presence or absence of progesterone or a progesterone analyte. In one non-limiting example, the one or more light sources are configured to illuminate the capture zone of an immunoassay device configured to detect for at least the presence or absence of progesterone or a progesterone analyte of the disclosure. The type of light source suitable for use with the immunoassay devices will depend on the chemistry of the immunoassay device. In one particular example, the one or more light sources are used to illuminate a detectable label provided by the immunoassay device configured to detect for at least the presence or absence of progesterone or a progesterone analyte. In a particular example, the detectable label provided on the immunoassay device is a fluorophore, and therefore, the one or more light sources of the reader device should include a fluorescent light source (e.g., a light-emitting diode (LED)). It is to be understood that the wavelength of light provided by the light source of the reader device should be selected based on the excitation wavelength of the detectable label, and can readily be selected by a person of skill in the art.

The reader may be configured to illuminate the capture zone and/or the control zone of an immunoassay device configured to detect for at least the presence or absence of progesterone or a progesterone analyte of the disclosure. For example, the reader may be configured to illuminate the first capture region configured to signal the presence or absence of progesterone or a progesterone analyte, the second capture region, the first control region, the second control region, or any combination thereof. In some cases, the reader is configured to scan across the test strip of an immunoassay device. In such cases where the immunoassay device utilizes a single fluorophore, the reader may contain a single fluorescent light source. In cases where the immunoassay device utilizes more than one fluorophore, the reader may contain more than one fluorescent light source.

The reader may further comprise one or more light detectors (e.g., a photodetector) for detecting optical signals from the immunoassay device. Generally speaking, the one or more light detectors should be capable of distinguishing between emitted light at a first discrete position and a second discrete position on the immunoassay device. This may be accomplished by, e.g., the one or more light sources scanning across the test strip of the immunoassay device and determining the position of the emitted light on the immunoassay device.

The diagnostic test device may further comprise a data analyzer. The data analyzer may have one or more processors configured to receive an optical signal. In some cases, the data analyzer is in operable communication with a reader device. The data analyzer may be configured to determine an amount of analytes present in a sample, for example, by measuring an amount of optical signal produced at the capture zone of an immunoassay device configured to detect for at least the presence or absence of progesterone or a progesterone analyte. For example, the data analyzer may be configured to calculate the area under the curve of a signal intensity plot. The data analyzer may further be configured to determine the differences between signal intensities among the multiple discrete regions on the test strip. For example, the data analyzer may be configured to determine the difference between the signal intensity at the first capture region and the signal intensity at the second control region. The data analyzer may further be configured to determine the difference between the signal intensity at the second capture region and the signal intensity at the first control region. The data analyzer may further be configured to calculate an amount or concentration of the analytes present in the sample. The data analyzer may be further configured to detect a binary optical pattern. The binary optical pattern can be generated by two fluorescent materials which excitation and/or emission spectrum differs in wavelength. In some cases, the binary optical pattern can be generated by one fluorescent material and one light absorbent material. The detection reagents may be conjugated with the two types of materials respectively and can be captured in the same capture zone, such that the capture zone may generate two different optical signal patterns in the data analyzer.

Figure 6:
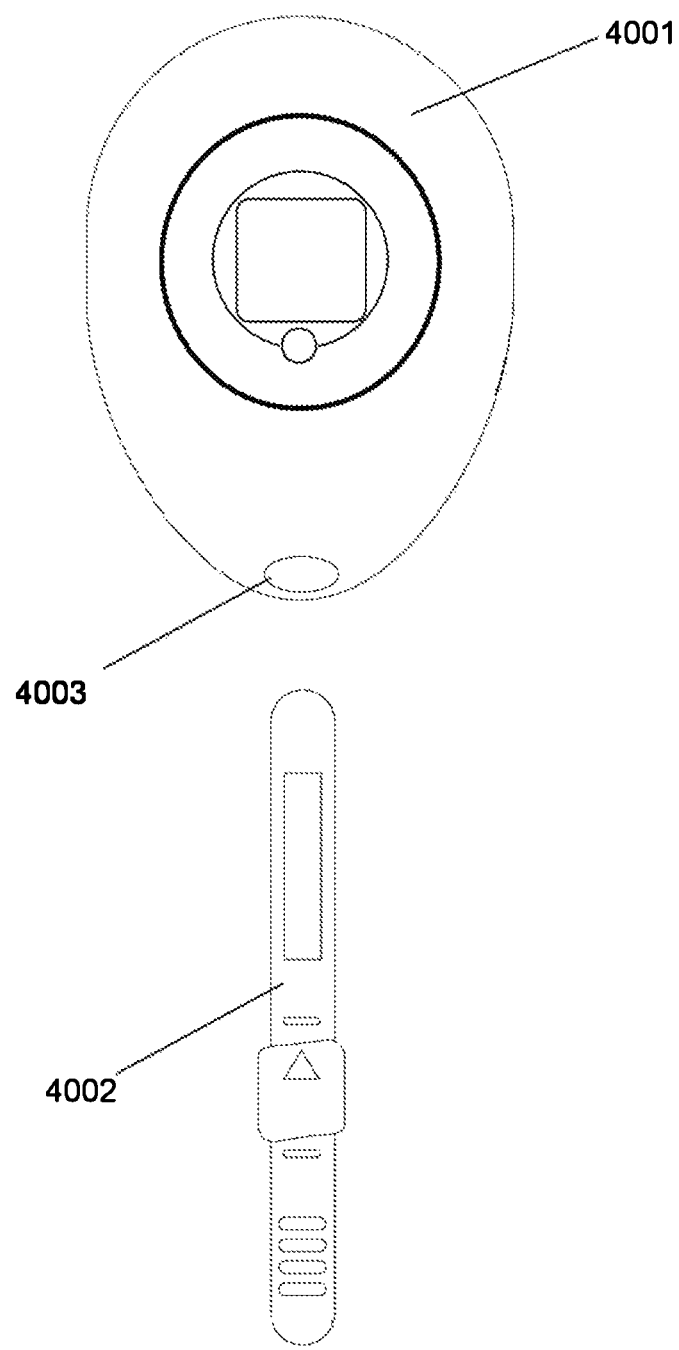
FIG. 6 depicts and embodiment of a test strip contained within a cartridge in exemplary use in association with a base unit.

In various aspects, the system may comprise a housing for containing the electronic components of the system such as that shown in FIGS. 5 and 6. The system may have a top housing and a bottom housing. The top housing may comprise a display module for displaying the results of an immunoassay configured to detect for at least the presence or absence of progesterone or a progesterone analyte as described herein. The system may further comprise a display cover. The system may further comprise a battery. The system may further comprise an optomechanics module. The optomechanics module may comprise the one or more light sources and one or more light detectors as described above. The system may further comprise a circuit board containing electronic components. The cassette or housing of the immunoassay test device configured to detect for at least the presence or absence of progesterone or a progesterone analyte may include a cavity. The chamber or receiving port of the diagnostic test system may include a ball bearing contained within the inner wall of the chamber. The ball bearing may hook or latch into the cavity of the test device, thereby locking the immunoassay test device configured to detect for at least the presence or absence of progesterone or a progesterone analyte into the receiving chamber of the diagnostic test system.

The diagnostic test system may include an optomechanics module comprising the one or more light sources for illuminating the test strip of the immunoassay device configured to detect for at least the presence or absence of progesterone or a progesterone analyte. The optomechanics module may be movable across an optical axis such that the optomechanics module moves laterally across the test strip of the immunoassay device configured to detect for at least the presence or absence of progesterone or a progesterone analyte, thereby scanning the test strip. The diagnostic test system may further comprise an actuation module. The actuation module may comprise one or more motors configured to actuate/move the optomechanics module. In some embodiments, the motors may be coupled to a rack and pinion mechanism that is configured to translate the optomechanics module along one or more directions. For example, the optomechanics module can be translated along a longitudinal axis of the test strip of the immunoassay device configured to detect for at least the presence or absence of progesterone or a progesterone analyte. The direction(s) of translation may or may not be orthogonal to an optical axis of the optomechanics module. The direction(s) of translation may be parallel to the longitudinal axis of the test strip, and the optical axis may be orthogonal to the longitudinal axis or a planar surface of the test strip. In some cases, the direction(s) of translation need not be parallel to the longitudinal axis of the test strip, and the optical axis need not be orthogonal to the longitudinal axis (or a planar surface) of the test strip. For example, the direction(s) of translation and/or the optical axis may be at an oblique angle relative to the longitudinal axis of the test strip.

In various aspects, the diagnostic test system may include an optical configuration suitable for use with the diagnostic test system and positioning of the optics above a test strip of an immunoassay device configured to detect for at least the presence or absence of progesterone or a progesterone analyte. The optical configuration may include a light source (e.g., a light-emitting diode (LED)) for illuminating the test strip. The optical configuration may further include one or more lens, a filter, a optical beamsplitters, or any combination thereof. The optical configuration may further include a photodetector for detecting an optical signal from the immunoassay device configured to detect for at least the presence of progesterone or a progesterone analyte. In an example, the system is configured to an excitation/emission spectra with an excitation wavelength of 492 nm and an emission wavelength of 512 nm.

In some cases, the diagnostic test device generates measurement results (e.g., concentration or relative amounts of analytes present in the sample) from a completed assay performed on the test device, as described throughout. In some cases, the diagnostic test device displays the measurement results on a screen contained within the device. Data containing the measurement results can be transmitted from the diagnostic test device to a mobile device and/or to a server. The data may be transmitted via one or more wireless or wired communication channels. The wireless communication channels may comprise Bluetooth®, WiFi, 3G, and/or 4G networks. The data containing the measurement results may be stored in a memory on the diagnostic test device when the diagnostic test device is not in operable communication with the mobile device and/or the server. The data may be transmitted from the diagnostic test device to the mobile device and/or the server when operable communication between the diagnostic test device and the mobile device and/or the server is re-established.

Further provided herein are kits which may include any number of immunoassay test devices configured to detect for at least the presence of progesterone or a progesterone analyte and/or reader devices of the disclosure. In one aspect, a kit is provided for determining qualitatively or quantitatively the presence of progesterone or a progesterone analyte and a second analyte in a biological sample, the kit comprising: a) an assay device configured to detect for at least the presence of progesterone or a progesterone analyte according to an embodiment of the disclosure; and b) instructions for using the kit.

In some cases, kits may include a one or more immunoassay test devices configured to detect for at least the presence of progesterone or a progesterone analyte of the disclosure. In some cases, the kit may provide a plurality of immunoassay devices configured to detect for at least the presence of progesterone or a progesterone analyte to enable a user to conduct a test on more than one occasion. In some cases, the immunoassay devices are configured for a single use (i.e., are disposable). A kit may include a plurality of test devices to enable a user to perform a test once a day, once every 2 days, once every 3 days, once every 4 days, once every 5 days, once every 6 days, once every week, once every 2 weeks, once every 3 weeks, once every 4 weeks, once every 5 weeks, once every 6 weeks once every 7 weeks, once every 8 weeks or more.

In some cases, kits may include a plurality of immunoassay devices, each capable of detecting at least the presence of progesterone or a progesterone analyte along with another analyte of the same type. In other cases, kits may include a plurality of immunoassay devices, each capable of detecting at least the presence of progesterone or a progesterone analyte and other different analytes. In a particular embodiment, a kit may include a plurality of immunoassay devices, each of the immunoassay devices capable of detecting the presence of progesterone or a progesterone analyte and LH in a biological sample. In another particular embodiment, a kit may include a plurality of immunoassay devices, each of the immunoassay devices capable of detecting the presence of progesterone or a progesterone analyte and hCG in a biological sample. In another particular embodiment, a kit may include a plurality of immunoassay devices, each of the immunoassay devices capable of detecting the presence of progesterone or a progesterone analyte and E2 in a biological sample. In another particular embodiment, a kit may include a plurality of immunoassay devices, each of the immunoassay devices capable of detecting the presence of progesterone or a progesterone analyte and FSH in a biological sample. In an embodiment, the immunoassay device may include progesterone or a progesterone analyte in addition to two or more of the additional hormones mentioned in this paragraph. Each of these configurations of immunoassay devices are described further in the present applicant's previous filings, including U.S. patent application Ser. No. 15/974,229, filed on May 8, 2018 claiming priority to U.S. Provisional Patent Application 62/503,223 Filed on May 8, 2017, a claim of priority made to each of which herein, and each of which are incorporated by reference in their entirety herein. These immunoassay devices are further described in U.S. patent application Ser. No. 16/381,229 filed Apr. 11, 2019, which is a national stage application of PCT Application No. PCT/US18/68027, filed Dec. 28, 2018, which is a PCT application claiming priority to U.S. Provisional Application No. 62/611,467 filed Dec. 28, 2017.

More specifically, the present inventor has recognized that due to the many drawbacks associated with serum testing for progesterone levels at one point in time as is commonly practiced, what is instead necessary to more effectively evaluate corpus luteum functionality involves a series of single tests to track progesterone levels (optionally, by evaluating analytes of progesterone in urine that correlate to serum progesterone levels) daily over a period of multiple days. To efficiently facilitate such testing, the method utilizes a number of single tests each configured to evaluate non-serum bodily fluids for the presence of at least progesterone or metabolites of progesterone above a pre-defined threshold level.

The non-serum bodily fluid evaluated via the preferred embodiment of the present invention is urine. To effectively facilitate the method when the non-serum bodily fluid tested is urine, the present inventor has discovered that the best time to collect a sample is immediately after the woman whose corpus luteum is under evaluation wakes up from the longest sleep period of the preceding 24 hours. The present inventor has noted that this sample consisting of the first morning urine presents a more accurate representation of the previous day's serum progesterone levels.

The present inventor has devised a method for determining functionality of the corpus luteum utilizing specialized testing devices, optionally single tests, depicted in FIG. 1. In various embodiments, the specialized testing devices evaluate non-serum bodily fluids for at least the presence of progesterone or at least one analyte of progesterone. In various embodiments, the testing devices are configured to detect for the presence of Pregnandiol Gluclorinide (PdG) in urine. In the preferred embodiment, the single tests comprise one or more test strips 3001 as further described in U.S. patent application Ser. No. 16/544,554 filed on Aug. 19, 2019, already incorporated by reference herein. In alternative embodiments, the single tests comprise devices to detect for the presence of progesterone in saliva, which optionally may consist of the testing devices described in United States Patent Application Publication US20180106799A1, which is incorporated by reference herein in its entirety. The present inventor has recognized that the methods contemplated herein, in an example, may be utilized in conjunction with a base unit configured read a single test configured to detect for the presence of progesterone in saliva.

The inventive method in its preferred form incorporates the step of predicting a date to optimally conduct testing 1001. In an example, the ovulation date is first estimated. During this step, the ovulation date is estimated by sampling cervical mucus, retrieving a basal body temperature, or utilizing lateral flow assays configured to detect for the presence of lutenizing hormone (LH) to predict ovulation. Optionally, the lateral flow assay may be configured as a test strip able to evaluate urine for the presence or absence of PdG on within multiple testing zones on the same strip. In an example, the estimated ovulation date is utilized to calculate the optimal date or range of dates to perform a test to evaluate a bodily fluid for the presence or absence of any of progesterone, PdG, LH, HcG or Estrogen. Optionally, the ovulation date is utilized to calculate the optimal date or range of dates to conduct bodily fluid testing.

Then, following the predicting an ovulation date step, the method preferably includes a collecting step 1002. During the collecting step 1002, a non-serum bodily fluid sample daily is collected for at least three consecutive days. In the case where the non-serum bodily fluid collected is urine, the sample may be collected within a cup during urination. In some instances, where the testing device is configured to allow the urine sample to be collected mid-stream during urination, the urine sample may be collected directly onto the testing device. In the preferred method where the non-serum bodily fluid collected is urine, the urine consists of a urine sample taken in the morning during the first urination after the subject awakens from overnight sleep or the longest sleep of the day (referred to as "first morning urine"). Alternatively, in the case where the non-serum bodily fluid sample collected is saliva, the sample may be collected with a swab. The collection step during the preferred method takes place between 7-10 days past the predicted ovulation date. In any case, the objective of the step is to collect enough of a sample to allow for the non-serum bodily fluid to be temporarily held as needed, and then evaluated by a testing device.

Then, following the collecting step 1002, a testing step 1003 takes place. During the testing step, for each non-serum bodily fluid sample, a testing device is used to evaluate the non-serum bodily fluid sample for the presence of progesterone or a metabolite of progesterone. In the preferred method, the testing step 1003 utilizes a single test consisting of a single-use disposable non-serum bodily fluid test configured to detect for at least progesterone or a metabolite of progesterone above a pre-defined threshold. In an embodiment of the invention, the non-serum bodily fluid test is configured to evaluate urine for the presence of at least one metabolite of progesterone, optionally PdG, above a threshold of 5 ug/mL. In an embodiment, the pre-defined threshold is determined from a value chosen from a sliding scale. In an embodiment, a threshold from within the scale's range is a value within the range of 3-10 ug/ml. During the testing step 1003, the single test indicates whether progesterone or a metabolite of progesterone is present in the tested non-serum bodily fluid sample above a pre-defined threshold. Optionally, the threshold amount may be set to the minimum amount of progesterone or progesterone analyte corresponding to the amount of minimum amount of progesterone needed to be present in the bloodstream to indicate that ovulation has occurred. A result indicated by the single test of "positive" means that the level of progesterone or analyte of progesterone present in the tested non-serum bodily fluid sample has exceeded the pre-defined threshold. A result indicated by the single test of "negative" means that the level of progesterone or analyte of progesterone present in the tested non-serum bodily fluid sample has not exceeded the pre-defined threshold. In an related example, a result indicated by the single test of "positive" could further indicate that the woman has entered into her infertile phase, and may thereby engage in sexual intercourse without the risk of unintended conception.

Then, following the first positive result indicated by the single test, indicating the presence of progesterone or a metabolite of progesterone above a pre-defined threshold in the tested non-serum bodily fluid sample, or the first fold change, a repeating step 1004 takes place. During the preferred method, the repeating step 1004, the collecting step 1002 and the testing step 1003 are performed over and over on a daily basis until the first negative result for progesterone or PdG displayed on the single test, indicating that progesterone or a metabolite of progesterone is below the pre-defined threshold. Alternatively the repeating step 1004 takes place daily for only 3 consecutive days, or for 4-10 days, regardless of the results displayed on the testing device. The present inventor has recognized that performing the repeating step 1004 multiple times during a fixed period of time, ideally a timeframe chosen from the range of 3-10 days, occasionally has the effect of mitigating errors displayed on the single test.

Following the conclusion of the repeating step 1004 or multiple repeating steps 1004, where one or more additional iterations of the collecting step 1002 and the testing step 1003 have taken place, a recording step 1005 takes place. During the recording step 1005, the total number of days that the single test has indicated a positive result for progesterone or PdG, each positive result indicating the presence of progesterone or a metabolite of progesterone above the pre-defined threshold at the time of testing, prior to the first negative result for progesterone or PdG displayed on the single test, is recorded. Such recordation may optionally take place with the assistance of a calendar or similar application operating on a mobile device. Such application may optionally also allow its user to record results for testing devices that evaluate bodily fluids for Lutenizing Hormone (LH), Follicle Stimulating Hormone (FSH), and/or Estrogen or Estrogen metabolites.

Figure 3:
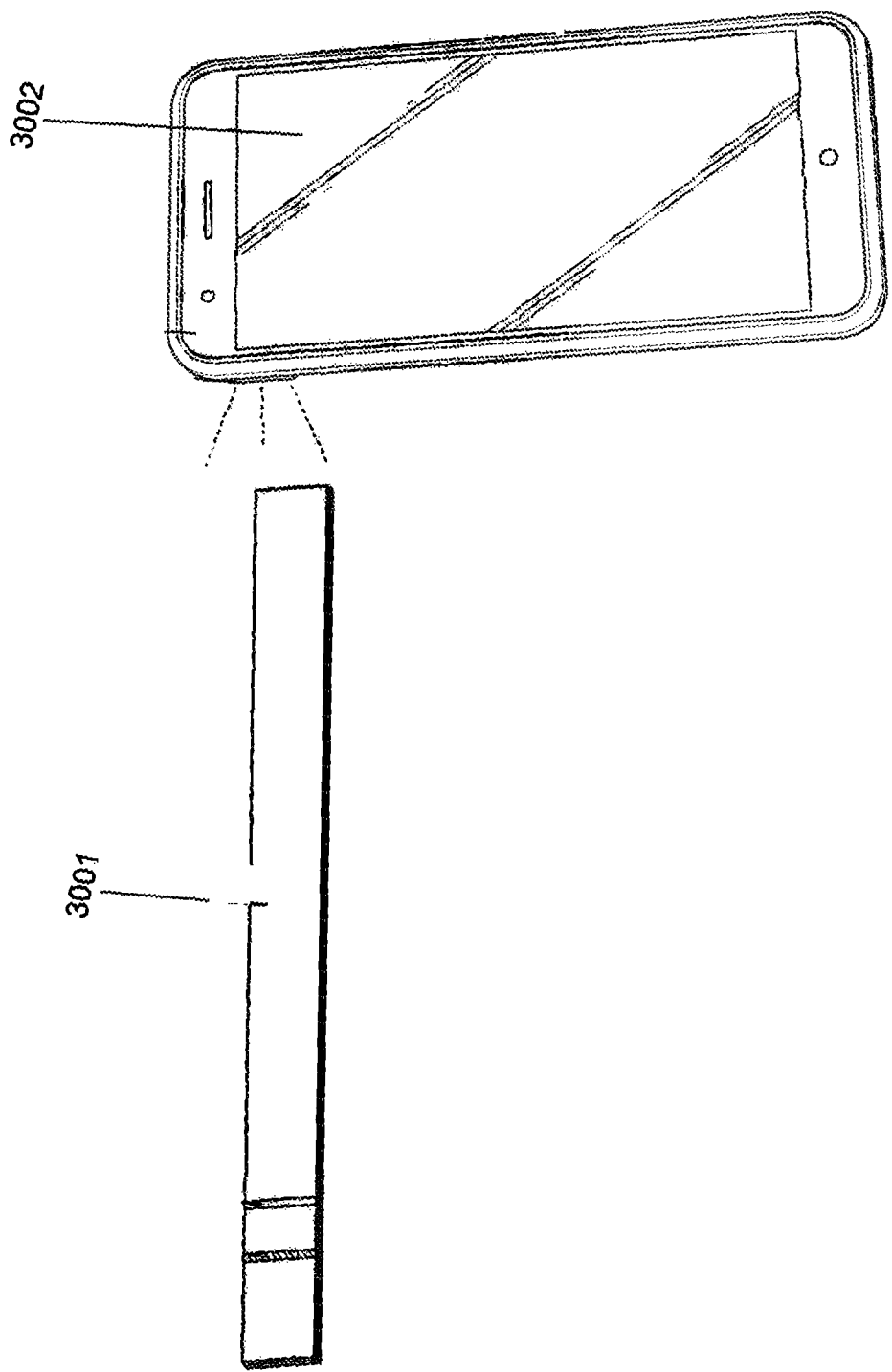
FIG. 3 depicts an embodiment featuring the use of an application operating on a mobile device featuring a camera.

The present inventor has noted that a mobile device operating an application featuring the ability to facilitate the recording step 1005 described above. In an example of the invention, an application operating on a mobile device featuring a camera, as depicted in FIG. 3, may be configured and utilized to photograph the results of a single test, and near-simultaneously interpret and record the results of each single test. The present inventor has noted that this example of the method is particularly helpful in instances where a single test incorporates one or more test strips 3001 configured to evaluate for multiple hormones and/or analytes, as is further described in U.S. patent application Ser. No. 16/381,229, filed on Apr. 11, 2019, incorporated by reference herein in its entirety. In one embodiment, the test strip used in accordance with the method described herein is configured to evaluate urine for the presence of PdG and LH.

Corpus luteum functionality and fertility and the fertile window within the menstrual cycle are closely related. In a related method, depicted in FIG. 2, following the step of collecting a single sample of urine 2001 optionally consisting of a woman urinating into a cup, a testing step 2002 follows. During an exemplary testing step, a single test configured to evaluate urine is placed into contact with the previously collected single sample of urine and utilized to detect for the whether both PdG and LH are present in the single sample of urine, each above a pre-defined threshold. Following the testing step, a step of determining whether ovulation has occurred 2003 follows. During an exemplary determining whether ovulation has occurred step, an indication on a single test that PdG exceeds a predefined threshold, optionally 5 ug/mL, signals that ovulation has occurred. In an example, the indication by the test strip 3001 that ovulation has occurred is presented by a visual label. In an example, the visual label is perceptible by the human eye. In an alternative example, the visual label consists of fluorescent dye imperceptible to the human eye readable only with the assistance of a machine, optionally a base unit 4001 or digital reader 3002. Following the determining whether ovulation has occurred step, a step of estimating the fertile window 2004 occurs. During an example of such step, the fertile window is estimated by calculating a number of days, optionally two days, following the first positive indication of LH after a negative indication for LH from the immediately preceding day's testing. The estimating the fertile window step also optionally comprises confirming a negative indication for PdG in urine, as a positive indication would signify that the fertile window has closed as the presence of PdG correlates to prior ovulation.

To further illustrate, in a series of tests associated with the methods described herein, if the following occurs, ovulation may be confirmed over a three tests on three separate days to aid in the estimation of the functionality of the corpus luteum and a prediction of the fertile window:

Example 1—test one results in readings of PdG below a pre-defined threshold and LH below a pre-defined threshold; test two results in PdG above a pre-defined threshold and LH above a pre-defined threshold; test three results in PdG above a pre-defined threshold and LH below a pre-defined threshold. This Example 1 signifies that following an LH surge indicating the follicle maturation, that progesterone released indicating ovulation. Such a result demonstrates proper corpus luteum functioning.

Example 2—test one, results in readings of PdG below a pre-defined threshold and LH below a pre-defined threshold; test two results in readings of PdG below a pre-defined threshold and LH a pre-defined threshold; test three results in readings of PdG a pre-defined threshold and LH above a pre-defined threshold. This Example 2 signifies that following a sustained LH surge indicating follicle maturation, that progesterone released indicating ovulation. Such a result demonstrates proper corpus luteum functioning.

Example 3—test one results in PdG below a pre-defined threshold and LH below a pre-defined threshold; test two results in PdG above a pre-defined threshold and LH below a pre-defined threshold. This Example 3 signifies that either the LH surge was missed by the test results or that urine was too diluted to detect the LH surge, but regardless that progesterone was released indicating ovulation. Such a result demonstrates proper corpus luteum functioning. Such result also highlights the importance of multiple day testing utilizing disposable test strips 3001 in accordance with the methods described herein as opposed to single point testing.

To further illustrate, in a series of tests, if the following occurs, a potential problem with the functionality of the corpus luteum may be detected:

Example 4—test one, results in readings of PdG below a pre-defined threshold and LH below a pre-defined threshold; test two results in readings of PdG below a pre-defined threshold and LH above a pre-defined threshold; test three results in readings of PdG below a pre-defined threshold and LH below a pre-defined threshold. Such a result indicates the possibility of improper corpus luteum functioning. As no progesterone (or its analyte, PdG) was detected during this exemplary series, it is possible that the relevant corpus luteum is not functioning properly to support implantation.

In embodiments of the invention, the tests utilized (optionally a "single test" which as used herein comprises one or more test strips 3001 that are disposable and altogether intended to be utilized one time to evaluate a single non-serum bodily fluid sample) incorporate a pre-defined threshold of PdG correlating in a positive result to at least the lowest amount of progesterone present and necessary to support conception. In embodiments of the invention, the tests utilized (optionally a single test) incorporate a pre-defined threshold of LH correlating in a positive result to at least the lowest amount of LH necessary to fully mature a follicle and cause rupture). In an embodiment of the invention, the pre-defined threshold of PdG is determined by a fixed amount of PdG antibody on the conjugate pad and the amount of PdG conjugate impregnated on the membrane in competitive assay form. In an embodiment of the invention, the pre-defined threshold of LH is determined by a fixed amount of LH antibody on the conjugate pad and the amount of LH antibody on the membrane in sandwich assay form. In an embodiment of the invention, the sandwich assay form and the competitive assay form are integrated together into a single test. In an embodiment of the invention, the receiving zones containing the LH antibody and the PdG antibody, and optionally antibodies of other hormones or analytes including FSH, Estrogen analyte, and hCG, are incorporated into a single conjugate pad within a single test. In an alternative embodiment of the invention, the receiving zones containing the LH antibody and the PdG antibody, and optionally antibodies of other hormones or analytes including FSH, Estrogen analyte, and hCG, are incorporated into at least two discrete conjugate pads within a single test. In an embodiment of the invention, the test strip 3001 is configured to incorporate multiple visual labels, including a test line 3003 and a visual label indicating the absence or presence of PdG 3006, a visual label indicating the absence or presence of LH, 3007, and a visual label indicating the absence or presence of estrogen or an analyte of estrogen 3008, as depicted in FIG. 4B. In an embodiment of the invention, the pre-defined threshold of PdG and/or the pre-defined threshold of LH is determined by a percentage difference from a previous test, optionally indicating a trend or fold change. In an embodiment, the test is contained within a cartridge. Optionally, the test or cartridge surrounding the test further incorporates an identifying feature, such as a QR Code, bar code or lot number, to identify the specific test and/or corresponding results. An example of such a single test incorporating such an identifying feature is further described in United States Patent Application Publication US 2018/0196037 A1 published on Jul. 12, 2018, which is hereby incorporated by reference in its entirety. In an embodiment, each conjugate pad may comprise antibodies conjugated to the same visual dye or different visual dyes.

In association with the above described method and other methods of use, a suitably configured single test able to detect for the presence of at least PdG or Progesterone in a bodily fluid is useful. Such a single test optionally comprises one or more test strips 3001 described with particularity in U.S. patent application Ser. No. 62/720,953, filed on Aug. 22, 2018; U.S. patent application Ser. No. 15/974,229 filed May 8, 2018; and U.S. patent application Ser. No. 16/381,229 filed Apr. 11, 2019; the entire contents of said applications hereby incorporated by reference. Referring now to FIG. 4, a test strip 3001 of the present invention is shown wherein an end with a sample pad is dipped into a urine sample such that the urine sample flows up the test strip 3001 in a direction depicted by an arrow and is stopped by an adsorbent pad at an end opposite the sample pad. The sample pad is readily available from various supplies, such as SureWick¬Æ Pad Materials from Millipore Sigma. The test strip 3001 includes a conjugate pad that can be a glass fiber conjugate pad saturated with colloidal gold, colored latex beads or other visual dye particles that are conjugated to anti-pregnanediol gluconoride mouse monoclonal antibodies. A membrane of the test strip 3001 can be a nitrocellulose membrane with pore size between 3 to 20¬μm. At least a test line configured to detect for the presence or absence of PdG in the tested fluid 3006 and a control line 3003 are impregnated on the membrane. The membrane is supported by a backing card.

The present inventor has discovered a unique combination of specific elements to allow for the detection of pregnanediol glucuronide (PdG) formulated such as to enable the creation of a pregnanediol urine test. In the preferred embodiment of the invention, Bovine Gamma Globulin (BGG) is conjugated with PdG and combined with a mouse anti-PdG antibody of IgG2b isotype binding partner. In an alternative embodiment of the invention Bovine Gamma Globulin (BGG) conjugated to PdG is combined with a mouse anti-PdG antibody of IgG1, IgG1 Kappa, IgG2a or IgG2c isotype. The present inventor has recognized that such a specific combination uniquely allows for colloidal gold to be conjugated to the anti-PdG antibody of one of the specific isotypes mentioned above, and for the colloidal gold conjugated anti-PdG antibody to interact with the PdG-BGG conjugate. Other combinations have been attempted, and have failed to allow the colloidal gold to function to produce the color needed to allow the test results to be viewable visually by the naked and untrained (layperson) eye. The present inventor has noted that the utilization of BGG conjugated to PdG allows for anti-PdG antibody, specifically of the IgG2b isotype, to bind in such a manner that colloidal gold is carried at a concentration sufficient for naked eye visualization. The present inventor has recognized the benefit associated with embodiments of the invention that a PdG test may be producible allowing the results to be visually interpreted with the naked eye.

The preferred embodiment of the invention relies on the certain reagents being able to interact with other reagents to produce color in the test zone of the membrane. Specifically, in the absence of PdG analyte in the urine sample, the following reagents must interact in order for the test results to be useful. First, in the preferred embodiment, colloidal gold must be conjugated to the anti-PdG antibody (in the preferred embodiment, anti-PdG antibody having the IgG2b isotype). In alternative embodiments, as a replacement for colloidial gold in other embodiments described herein, an alternative visual dye such as latex beads may be utilized to a similar effect. Further, in embodiments of the invention, the colloidal gold conjugated anti-PdG antibody must interact with the PdG-BGG conjugate. Moreover, the PdG-BGG must bind the nitrocellulose membrane. The present inventor has recognized that for these embodiments to function as intended, these interactions between and among the colloidal gold conjugated anti-PdG antibody and the PdG-BGG conjugate must be strong enough and stable enough to form and stay bound during urine sample application and lateral flow of urine across the reaction zone to solve the problems faced by the suboptimal prior art mechanisms. In an embodiment configured to evaluate urine for hormones and/or analytes other than PdG in addition to PdG, a visual label having a distinct color is utilized to identify for the presence of each hormone and/or analyte tested. In one particular embodiment, a colloidal gold conjugated anti-PdG antibody is utilized to display or omits the color red to indicate the absence or presence of PdG within a sample and a latex bead conjugated anti-LH antibody is utilized to display or omit the color blue to indicate the absence or presence of LH within the same urine sample on the same test strip. In an embodiment, a test strip configured to evaluate urine for the presence of PdG and LH is contained within a cassette. In an embodiment, also further described in U.S. patent application Ser. No. 15/974,229, filed on May 8, 2018, incorporated by reference in its entirety herein, a disposable lateral flow assay tests cassette is configured to allow the sample to permeate through the one or more test strips 3001 into or through one or more detection zones, each optionally comprising a reagent-impregnated membrane, contained within each test strip. In an embodiment of the invention, the test strip in its novel configuration as described elsewhere herein is contained within a cartridge (also referred to as a "detection device"), and configured to be read within an associated base unit (also referred to as a "detection instrument") as further described within U.S. patent application Ser. No. 16/302,085, filed on Jul. 11, 2019, which is hereby incorporated by reference herein in its entirety. In an embodiment of the invention, the base unit consists of the diagnostic test system as described in International Patent Application PCT/CN2017/095452 filed on Aug. 1, 2017 and in International Publication Number WO 2019/023926 A1, which are hereby incorporated by reference in its entirety.

An embodiment of the present invention comprises a testing system to detect the presence of PdG optimized for visual detection by a layperson's, or non-expert's, naked eye utilizing the embodiment in other than a laboratory context. The present inventor has recognized that in embodiments of the invention, the combination of mouse anti-PdG IgG1, IgG2a, IgG2b, and/or the IgG2c antibody conjugated to a visual label, such as colloidal gold and/or latex beads, and PdG conjugated to BGG carrier protein create sufficient binding partners. Resultantly, the preferred embodiment of the invention comprises a visual test readable by the untrained eye in a context outside of a laboratory environment, as depicted in FIGS. 4A-4B. In an embodiment, the visual label comprises colloidal gold 40 nm particles having an absorbance of 520-540 nm.

In varying embodiments of the invention, the visual label comprises particles having an absorbance of 380-750 nm which the present inventor notes is the approximate range typically perceptible to the human eye. In an alternative embodiment, the visual label comprises a fluorescent dye. In an embodiment, the fluorescent dye is readable only with the assistance of a machine configured to detect wavelengths on the visual spectrum outside of the range perceptible by the human eye. In one embodiment, the visual label comprises In an embodiment, the visual label comprises colloidal gold 40 nm particles having an absorbance of 520-540 nm.

As noted elsewhere in this application, the visual label in embodiments of the invention comprise particles having an absorbance of 380-750 nm which the present inventor notes is the approximate range typically perceptible to the human eye. In an alternative embodiment, the visual label comprises a fluorescent dye. In an embodiment, the configuration of the test strip and optionally a corresponding base unit are configured to allow for the interpretation of the results of the strip to indicate for the presence or absence of progesterone or analytes of progesterone due to the unique and novel configurations disclosed herein conjugated with a fluorescent label. An example of a lateral flow assay utilizing such a fluorescent dye label is described further in U.S. patent application Ser. No. 11/974,358, filed on Oct. 12, 2007, which is hereby incorporated by reference in its entirety. In an embodiment of the test strip, the visual label comprises particles having an absorbance of 190-380 nm, which the present inventor notes is the ultraviolet region imperceptible to the human eye. In an embodiment, the fluorescent dye is readable only with the assistance of a machine configured to detect wavelengths on the visual spectrum outside of the range perceptible by the human eye, which in an example is further described in U.S. patent application Ser. No. 11/974,358 mentioned above. The test results featuring a visual label imperceptible to the human eye of a test strip 3001 are optionally determinable by ultraviolet visible spectroscopy. In one embodiment, the device configured to interpret the results of a test strip featuring a visual label imperceptible to the human eye consists of a base unit 4001. In an alternative embodiment, the test results are interpreted with the assistance of a digital reader 3002. In an embodiment of the invention, the digital reader 3002 comprises a mobile phone or smartphone device as depicted in FIG. 3. In an embodiment, the smartphone device is configured with an application configured to collect, store and via the display of the smartphone device present the results of one or more lateral flow assays photographed and interpreted via a smartphone in association with the application.

In association with the methods described herein, a system comprising an application configured to operate on a mobile computing device comprising a camera, storage, display and processing mechanisms, such as a computer processor is utilized to perform the associated steps. In an embodiment, the application incorporates features to interpret the results of a urine test strip configured to detect LH, E3G and PdG in urine above or below a pre-defined threshold. The application is configured to photograph a test strip via the camera of the mobile computing device and then interpret the results via processing mechanisms of the mobile computing device to determine the indication of a positive or negative result for each LH, E3G and PdG, independently. In an embodiment of the invention, the mobile computing device can further photograph and provide an indication for a positive or negative result for FSH. In varying embodiments, in association with the methods described herein, the results are either collected with the result associated with one hormone or analyte (i.e. LH, E3G, PdG, FSH) collected on one lateral flow assay, or alternatively collected with the result associated with multiple hormones or analytes (i.e. LH, E3G, PdG, FSH) together on the same lateral flow assay, or some combination thereof.

The application is further configured to record and store the results of each test in a series. In an embodiment, the application generates a notice to a user to prompt the user to initiate and utilize the application to evaluate a new test, optionally a lateral flow assay as described elsewhere herein, on a daily basis, optionally in association with the methods taught elsewhere herein. In various embodiments, the storage may exist on the mobile computing device (i.e. smartphone or mobile phone) itself or via a communicatively connected storage device, such as, for example, cloud connected storage. The application is configured to present a graph of the results over a time series on the display of the mobile computing device. The application is further configured to package the results for transfer to a healthcare provider in an interoperable format applicable to uses associated with medical information, such as a continuity of care record and/or HL 7. The application in an embodiment incorporates a functionality to enable telemedicine, via a button to initiate a video chat with a healthcare provider or a phone call with a healthcare provider in association with the transfer of the relevant information to the healthcare provider.

In an embodiment, the application utilizes the detected hormonal levels or trends of hormonal levels to generate suggestions of lifestyle changes applicable to the subject user of the urine test strips. The suggested treatment protocols in one example are delivered to a healthcare professional. In other examples, the suggested treatment protocols are delivered to the user of the application or both the user of the application and one or more healthcare providers. In various embodiments, educational information associated with hormonal deficiencies and peri-menopause may be generated based on the results of each strip or the detected trends of hormonal concentrations.

In an embodiment, the application utilizes the results to detect trends of hormonal concentrations. The trends may thereby be interpreted by the application to generate suggested treatment protocols. In an embodiment, the application utilizes the detected hormonal levels or trends of hormonal levels to generate suggestions of diet changes applicable to the subject whose urine is under evaluation by the lateral flow assays in association with the methods described elsewhere herein. For example, the ingestion of certain seeds is well known in the art to regulate or affect the hormone levels of a person who ingests such seeds. In an embodiment, the application is configured to generate suggestions for the consumption of certain seeds to affect hormonal concentrations of the subject user of one or more lateral flow assays. In an embodiment, a prompt to purchase or subscribe to the purchase one or more products containing the suggested amount of seeds to ingest based on the results of one or more of the lateral flow assays is shown on the display by the application in conjunction with the suggested diet change and/or the interpretation of the results of one or more lateral flow assays as described elsewhere herein.

The present inventor has noted that the utilization of this newly discovered system allows for monitoring of hormonal concentrations in association with menopause tracking to be done consistently from cycle to cycle to ensure efficacy of treatment regimens, such as the seed consumption, dietary or lifestyle changes, further communication with medical professionals (optionally via telemedicine communications) or prompts to read further educational materials as described elsewhere herein. Moreover, such consistent tracking allows a subject user to identify hormone pattern changes that may cause symptoms to occur earlier for faster and/or more tailored treatment, optionally in association with the treatment of symptoms related to menopause. As such, the methods described herein may further comprise the steps of detecting trends of hormonal concentrations, identifying hormonal concentrations associated with menopause from the one or more lateral flow assays, and suggesting treatment protocols, optionally the consumption of certain seeds at varying times, diet changes, consultation with healthcare providers via telemedicine appointments and/or lifestyle changes, as described elsewhere herein. In an embodiment, such steps are performed in association with the operation of an application in association with a smartphone device as described elsewhere herein.

The methods disclosed herein comprise one or more steps or actions for achieving the described method. The method steps and/or actions may be interchanged with one another without departing from the scope of the claims. The order and/or use of specific steps and/or actions may be modified without departing from the scope of the claims.

It is to be understood that the claims are not limited to the precise configuration and components illustrated above. Various modifications, changes and variations may be made in the arrangement, operation and details of the methods and apparatus described above without departing from the scope of the disclosure.

While the foregoing is directed to aspects of the present disclosure, other and further aspects of the disclosure may be devised without departing from the basic scope thereof.

The invention claimed is:

1. A method for evaluating urine of a subject to estimate the fertile window, comprising:
   collecting a single sample of urine,
   testing the single sample of urine with one or both of a first lateral flow assay and a second lateral flow assay, the first lateral flow assay comprising:
      a sample pad configured to receive the urine sample,
      a receiving zone within a conjugate pad, the conjugate pad saturated with a conjugate comprising an anti-PdG antibody conjugated to a visual label in a concentration selected from the range inclusive of 1-10 µg/ml,
      a membrane comprising a testing zone,
      the testing zone comprising PdG conjugated to a carrier protein that binds PdG antigens at 8-32 molecules per carrier protein, and
      further configured to evaluate for the presence or absence of PdG at or above a PdG threshold, the PdG threshold selected from within the range inclusive of 3-20 µg/ml,
      the membrane further configured to provide an observable positive result for the presence of PdG in the sample of urine at the PdG threshold as indicated by the absence of the color of the visual label in the testing zone following the operation of the first lateral flow assay,
   the second lateral flow assay comprising:
      a sample pad configured to receive the urine sample,
      a receiving zone within a conjugate pad, the conjugate pad saturated with a conjugate, the conjugate comprising an anti-LH antibody conjugated to a visual label,
      a membrane comprising a testing zone,
      the testing zone comprising LH conjugated to a carrier protein and further configured to evaluate for the presence or absence of LH at a LH threshold of no less than 20 ml U/ml,
      the membrane configured to provide an observable positive result for the presence of LH in the sample of urine at a LH threshold as indicated by the presence of the color of the visual label in the testing zone following the operation of the second lateral flow assay
   determining that ovulation has occurred and that the fertile window has closed by a positive result for the presence of PdG at the PdG threshold or determining that the fertile window has opened by observing a positive result for the presence of LH at or above the LH threshold, and
   estimating the fertile window dates, optionally by repeating the collecting, testing and determining steps, the fertile window opening date of the subject estimated as the date of the first positive result in a menstrual cycle of the subject for the presence of LH at or above the LH threshold and the fertile window closing date of the subject estimated as the date of the first positive result in the menstrual cycle for the presence of PdG at the PdG threshold, following the evaluation of at least one result for the presence or absence of LH at or above the LH threshold and at least one result for the presence or absence of PdG at the PdG threshold during the menstrual cycle.

2. The method of claim 1, the first lateral flow assay further comprising:
the receiving zone additionally saturated with a second conjugate,
the second conjugate comprising an anti-estrone-3-glucuronide antibody conjugated to a visual label,
the membrane comprising a second testing zone,
the second testing zone comprising estrone-3-glucuronide conjugated to a carrier protein, and further configured to evaluate for the presence or absence of estrone-3-glucuronide, and
the membrane further configured to provide an observable positive result for the presence or absence of estrone-3-glucuronide at the estrone-3-glucuronide threshold as indicated by the visual label in the testing zone following the operation of the first lateral flow assay.

3. The method of claim 2, the determining step further comprising:
determining that the fertile window has opened by observing a positive result for the presence of estrone-3-glucuronide.

4. The method of claim 1, the first lateral flow assay or the second lateral flow assay further comprising:
the receiving zone additionally saturated with a second conjugate,
the second conjugate comprising an anti-estrone-3-glucuronide antibody conjugated to a visual label,
the membrane comprising a second testing zone,
the second testing zone comprising estrone-3-glucuronide conjugated to a carrier protein, and further configured to evaluate for the presence or absence of estrone-3-glucuronide at or above an estrone-3-glucuronide threshold,
the membrane further configured to provide an observable positive result for the presence or absence of estrone-3-glucuronide at the estrone-3-glucuronide threshold as indicated by the visual label in the testing zone following the operation of the first lateral flow assay comprising the second conjugate comprising an anti-estrone-3-glucuronide antibody conjugated to a visual label or the second lateral flow assay comprising the second conjugate comprising an anti-estrone-3-glucuronide antibody conjugated to a visual label.

5. The method of claim 4, the determining step further comprising:
determining that the fertile window has opened by observing a positive result for the presence of estrone-3-glucuronide.

6. The method of claim 1, the determining step further comprising:
the positive result for the presence of PdG at the PdG threshold obtained by an optical reader, and
the positive result for the presence of LH at or above the LH threshold obtained by an optical reader.

7. The method of claim 1, the determining step further comprising:
the result for the presence of PdG at or above the PdG threshold obtained by photographing a diagnostic test with the camera of a smartphone, and
the result for the presence of LH at or above the LH threshold obtained by photographing a diagnostic test with the camera of a smartphone.

8. The method of claim 7, the smartphone further configured to utilize an application to collect, store and upon a display of the smartphone present the result for the presence of PdG at or above the PdG threshold and the result for the presence of LH at or above the LH threshold.

* * * * *